US012577191B2

(12) United States Patent
Kim et al.

(10) Patent No.: US 12,577,191 B2
(45) Date of Patent: *Mar. 17, 2026

(54) BATCH PREPARATION METHOD OF ESTER-BASED MATERIAL

(71) Applicant: LG CHEM, LTD., Seoul (KR)

(72) Inventors: Hyun Kyu Kim, Daejeon (KR); Jeong Ju Moon, Daejeon (KR); Eun Suk Kim, Daejeon (KR); Yun Gon Heo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 496 days.

This patent is subject to a terminal disclaimer.

(21) Appl. No.: 18/015,640

(22) PCT Filed: Sep. 17, 2021

(86) PCT No.: PCT/KR2021/012894

§ 371 (c)(1),
(2) Date: Jan. 11, 2023

(87) PCT Pub. No.: WO2022/065851

PCT Pub. Date: Mar. 31, 2022

(65) Prior Publication Data

US 2023/0303475 A1     Sep. 28, 2023

(30) Foreign Application Priority Data

Sep. 24, 2020    (KR) ........................ 10-2020-0124124
Sep. 17, 2021    (KR) ........................ 10-2021-0124973

(51) Int. Cl.
    *C07C 67/08*        (2006.01)
    *C07C 67/48*        (2006.01)
(52) U.S. Cl.
    CPC .............. *C07C 67/08* (2013.01); *C07C 67/48* (2013.01)

(58) Field of Classification Search
    CPC ......... C07C 67/08; C07C 67/48; C07C 67/56; C07C 67/58; C07C 69/80; C07C 69/82; C07C 69/76
    See application file for complete search history.

(56) References Cited

U.S. PATENT DOCUMENTS

| | | | |
|---|---|---|---|
| 5,532,405 | A | 7/1996 | Lyford, IV |
| 6,355,817 | B1 | 3/2002 | Woods et al. |

(Continued)

FOREIGN PATENT DOCUMENTS

| | | |
|---|---|---|
| CA | 2010062 C | 2/1999 |
| CN | 1291180 A | 4/2001 |

(Continued)

OTHER PUBLICATIONS

Chinese Office Action dated Jun. 20, 2024, issued in corresponding Chinese Patent Application No. 202180060622.1.

(Continued)

*Primary Examiner* — Yate' K Cutliff
(74) *Attorney, Agent, or Firm* — Morgan, Lewis & Bockius LLP

(57)                    ABSTRACT

The present invention provides a method for preparing an ester-based material, the method including a step in which in a batch reactor, under a catalyst, at least one polycarboxylic acid selected from the group consisting of a terephthalic acid, a phthalic acid, an isophthalic acid, a cyclohexane dicarboxylic acid, a cyclohexane tricarboxylic acid, a trimellitic acid, and citric acid reacts with at least one monoalcohol having 3 to 12 alkyl carbon atoms, wherein pressure in the reactor is configured such that the pressure at the early stage is 0.3 barg to 1.0 barg and the pressure at the latter stage is 0 barg to 0.5 barg, the pressure at the early stage being greater than the pressure at the latter stage, and the (Continued)

early and latter stages are divided based on any one of the time points when reaction conversion rate is 30% to 90%.

10 Claims, 1 Drawing Sheet

(56) References Cited

U.S. PATENT DOCUMENTS

| | | | |
|---|---|---|---|
| 7,385,075 B2 * | 6/2008 | Disteldorf | C07C 67/54 |
| | | | 560/89 |
| 2002/0086969 A1 | 7/2002 | DeBruin | |
| 2002/0087028 A1 | 7/2002 | Hirata et al. | |
| 2002/0091227 A1 | 7/2002 | DeBruin | |
| 2002/0137877 A1 | 9/2002 | Debruin | |
| 2004/0030175 A1 | 2/2004 | Disteldorf et al. | |
| 2004/0187080 A1 | 9/2004 | Brooke et al. | |
| 2010/0137631 A1 * | 6/2010 | De Munck | C07C 67/303 |
| | | | 560/99 |
| 2017/0297998 A1 | 10/2017 | Schraut et al. | |
| 2018/0002268 A1 | 1/2018 | Kim et al. | |
| 2019/0263745 A1 | 8/2019 | Lee et al. | |
| 2021/0040026 A1 | 2/2021 | Lee et al. | |

FOREIGN PATENT DOCUMENTS

| | | | |
|---|---|---|---|
| CN | 105579430 A | 5/2016 | |
| EP | 0383405 A1 | 8/1990 | |
| EP | 3 342 813 A1 | 7/2018 | |
| JP | H9-003003 A | 1/1997 | |
| JP | 2004-513160 A | 4/2004 | |
| JP | 2010-520944 A | 6/2010 | |
| JP | 2012-250915 A | 12/2012 | |
| JP | 2013-159756 A | 8/2013 | |
| KR | 10-2000-0023419 A | 4/2000 | |
| KR | 10-2000-0023420 A | 4/2000 | |
| KR | 10-2003-0048469 A | 6/2003 | |
| KR | 10-2003-0068171 A | 8/2003 | |
| KR | 10-2014-0077342 A | 6/2014 | |
| KR | 10-1663586 B1 | 10/2016 | |
| KR | 10-2019-0027622 A | 3/2019 | |
| KR | 10-2019-0027623 A | 3/2019 | |
| TW | 201704198 A | 2/2017 | |
| WO | 02/38531 A1 | 5/2002 | |
| WO | 2015/045969 A1 | 4/2015 | |
| WO | WO 2015045969 * | 4/2015 | C07C 67/08 |

OTHER PUBLICATIONS

Rahman et al., "The plasticizer market: an assessment of traditional plasticizers and research trends to meet new challenges," Progress in Polymer Science, 29: 1223-1248 (2004).

Janjua et al., "Systemic Uptake of Diethyl Phthalate, Dibutyl Phthalate, and Butyl Paraben Following Whole-Body Topical Application and Reproductive and Thyroid Hormone Levels in Humans," Environmental Science and Technology, 41: 5564-5570 (2007).

International Search Report (with partial translation) and Written Opinion dated Jan. 12, 2022, for corresponding International Patent Application No. PCT/KR2021/012894.

Office Action dated Sep. 25, 2024 issued in corresponding Taiwanese Patent Application No. 11320979320.

Office Action issued Jan. 9, 2024 for Japanese Patent Application No. 2023-502829.

Extended European Search Report issued Mar. 7, 2024 for European Patent Application No. 21872879.8.

Office Action dated Dec. 22, 2025 issued in corresponding Indian Patent Application No. 202317010062.

* cited by examiner

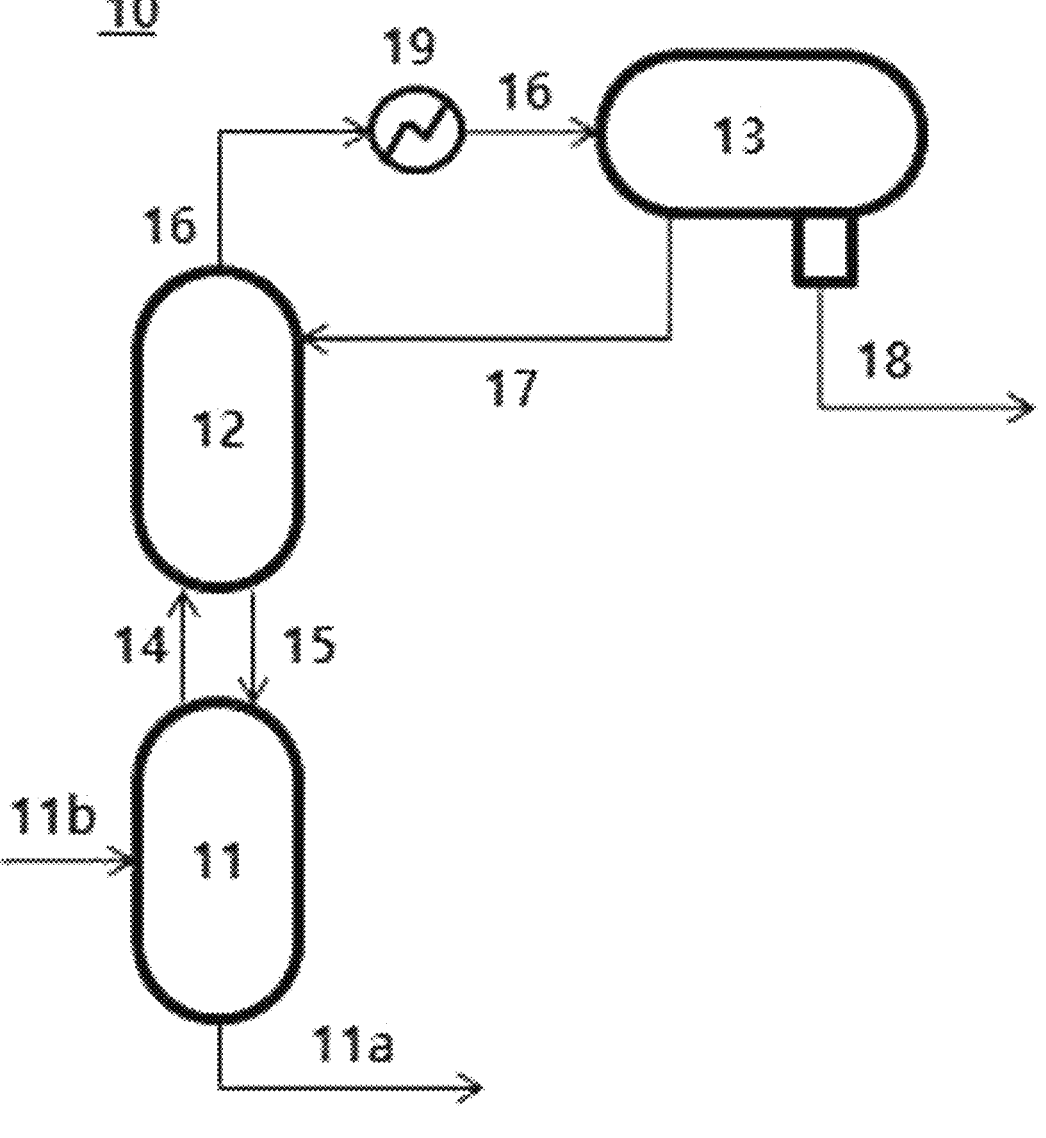

BATCH PREPARATION METHOD OF ESTER-BASED MATERIAL

CROSS-REFERENCE TO RELATED APPLICATIONS

This application claims the benefit of Korean Patent Application Nos. 10-2020-0124124, filed on Sep. 24, 2020, and 10-2021-0124973 filed on Sep. 17, 2021, in the Korean Intellectual Property Office, the disclosures of which are incorporated herein in their entireties by reference.

TECHNICAL FIELD

Technical Field

The present invention relates to a batch preparation method of an ester-based material, the method configured to control the pressure of a reactor in the batch-wise preparation of the ester-based material.

BACKGROUND ART

Phthalate-based plasticizers had accounted for 92% of the global plasticizer market by the 20th century (see Mustafizur Rahman and Christopher S. Brazel, "The plasticizer market: an assessment of traditional plasticizers and research trends to meet new challenges", Progress in Polymer Science 2004, 29, 1223-1248), and are additives used for imparting flexibility, durability, and cold resistance mainly to polyvinyl chloride (hereinafter referred to as PVC) and lowering the viscosity during melting to improve processability. These phthalate-based plasticizers are added in various amounts to PVC and widely used in various applications from rigid products such as rigid pipes to soft products which may be used for such as food packaging materials, blood bags, flooring materials, etc. due to their soft and good flexibility, and thus are more closely related to real life than any other material, and the direct contact with the human body may not avoidable.

However, despite the compatibility of the phthalate-based plasticizers with PVC and their excellent capability to impart flexibility, it has been argued recently about harmfulness of the PVC product containing the phthalate-based plasticizers that the phthalate-based plasticizers may leak out of the PVC product when used in real life, and act as a presumed endocrine disrupting (environmental hormone) substance and a carcinogen of the level of heavy metals (see N. R. Janjua et al., "Systemic Uptake of Diethyl Phthalate, Dibutyl Phthalate, and Butyl Paraben Following Whole-body Topical Application and Reproductive and Thyroid Hormone Levels in Humans", Environmental Science and Technology 2007, 41, 5564-5570). Especially, since the report about the leakage of di-(2-ethyl hexyl) phthalate (DEHP), which was the most used phthalate-based plasticizer in the US in the 1960s, out of the PVC product, the interest in environmental hormones has been added in the 1990s and global environmental regulations as well as extensive studies on hazards of the phthalate-based plasticizers to human have started.

Therefore, in order to cope with environmental hormone issues and environmental regulations due to the leakage of the phthalate-based plasticizers, particularly di(2-ethylhexyl) phthalate, a number of researchers have been conducting research to develop a new, alternative, non-phthalate-based plasticizer which is free of phthalic acid used in the production of di(2-ethylhexyl) phthalate, a phthalate-based plasticizer which is phthalate-based but free of the leakage of plasticizers to be used for industrial purposes instead of di(2-ethylhexyl) phthalate, or a leakage inhibition technology which may inhibit the leakage of the phthalate-based plasticizers to greatly reduce the hazards to human and be in accordance with environmental standards.

Accordingly, as ester-based plasticizers, materials which are free of environmental issues and thus may replace di(2-ethylhexyl) phthalate causing typical environmental issues have been under active development, and researches on the development of an ester-based plasticizer having excellent physical properties, as well as researches on facilities for preparing such the ester-based plasticizer have been actively conducted. In terms of process design, more efficient, economical, and simple process design has been required.

Meanwhile, batch processing is most widely applied in industrial sites as a process of preparing the above ester-based plasticizer, and as a batch process, inventions such as a gas-liquid separation system for reflux of unreacted substances in a reactor and efficient removal of side reactants (Korean Patent Application Laid-Open No. 10-2019-0027622) and a system integrating facilities of a primary direct esterification reaction and a secondary trans esterification reaction for simpler batch process facilities (Korean Patent Application Laid-Open NO. 10-2019-0027623) have been introduced.

However, the batch processes introduced in such inventions are designed to enhance reactions through simplified or modified facilities, and thus are too costly to be applicable in industry due to addition of facilities or change of lines over processes. Thus, there remains a need for developing a process ensuring that reactions are optimized through alteration and control of process conditions.

RELATED ART DOCUMENT (Patent Document 1) Korean Patent Laid-Open Publication No. 10-2019-0027622

(Patent Document 2) Korean Patent Laid-Open Publication No. 10-2019-0027623

(Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

The present invention is to provide a method for preparing an ester-based material, the method appropriately controlling pressure inside a reactor at the initiation of a reaction and in the course of a reaction to achieve high conversion rate and ensure uniformity of product quality, and maximizing productivity through reduced reaction duration while saving energy consumption through reduced reflux.

Technical Solution

To solve the tasks, the present invention provides a method for preparing an ester-based material.

(1) The present invention provides a method for preparing an ester-based material, the method including a step in which in a batch reactor, under a catalyst, at least one polycarboxylic acid selected from the group consisting of a terephthalic acid, a phthalic acid, an isophthalic acid, a cyclohexane dicarboxylic acid, a cyclohexane tricarboxylic acid, a trimellitic acid, and citric acid reacts with at least one mono-alcohol having 3 to 12 alkyl carbon atoms, wherein pressure in the batch reactor is configured such that the pressure at the early stage is 0.3 barg to 1.0 barg and the pressure at the latter stage is 0 barg to 0.5 barg, the pressure at the early stage being greater than the pressure at the latter stage, and the early and latter stages are divided based on any one of the time points when reaction conversion rate is 30% to 90%.

(2) The present invention provides the method according to (1) above, wherein the batch reactor has an early stage pressure of 0.4 barg to 1.0 barg, and a latter stage pressure of 0 barg to 0.4 barg.

(3) The present invention provides the method according to (1) or (2) above, wherein the mono-alcohol is added in excess of 20 mol % to 100 mol % relative to polycarboxylic acid equivalent.

(4) The present invention provides the method according to any one of (1) to (3) above, wherein the reaction is performed in the presence of a catalyst, and the catalyst is added at one or more points before the initiation of the reaction and in the course of the reaction.

(5) The present invention provides the method according to any one of (1) to (4) above, wherein the catalyst is added before the initiation of the reaction and in the course of the reaction.

(6) The present invention provides the method according to any one of (1) to (5) above, wherein the latter stage pressure gradually decreases as reactions proceed.

(7) The present invention provides method according to any one of (1) to (6) above, wherein the method further includes adding an additional amount of the mono-alcohol in the course of reactions.

(8) The present invention provides the method according to any one of (1) to (7) above, wherein the preparation method is performed in a reaction unit including: a reactor in which an esterification reaction of a polycarboxylic acid with mono-alcohol is performed; a column in which mono-alcohol and water vaporized upon the esterification reaction are introduced from the reactor to perform gas-liquid separation, and liquid is fed into the reactor at a lower portion and gas is discharged from the top; a condenser liquefying the gas discharged from the top of the column, which is then converted into a liquid mixture; and a layer separator in which the liquid mixture is layer-separated into an organic layer and an aqueous layer, and the separated organic layer is fed to an upper end of the column.

(9) The present invention provides the method according to any one of (1) to (8) above, wherein the reaction unit further includes a pre-mixer placed upstream of the reactor; and the polycarboxylic acid and the mono-alcohol are fed into to the pre-mixer, mixed and preheated, and then transferred to the reactor.

(10) The present invention provides the method according to any one of (1) to (9) above, wherein the catalyst is added through at least one selected from among the reactor, the pre-mixer, and the liquid from the column.

Advantageous Effects

The present invention, in the preparation of an ester-based material, separates the early stage and the latter stage of reactions based on a specific time point and controls pressure in a reactor based on the determined time, and thus may minimize the reflux amount of alcohol, save energy consumption through reduced reaction duration, and maximize the productivity of the ester-based material.

BRIEF DESCRIPTION OF THE DRAWINGS

The FIGURE is a process view showing a reaction unit applied to the present invention.

MODE FOR CARRYING OUT THE INVENTION

Hereinafter, the present invention will be described in detail to aid in understanding of the present invention.

It will be understood that words or terms used in the description and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

According to an embodiment of the present invention, a batch method for preparing an ester-based material is performed in a reaction unit including a batch reactor, a column for a reflux system, a bed separator, and a condenser.

In addition, the preparation method includes a step in which in a batch reactor, under a catalyst, at least one polycarboxylic acid selected from the group consisting of a terephthalic acid, a phthalic acid, an isophthalic acid, a cyclohexane dicarboxylic acid, a cyclohexane tricarboxylic acid, a trimellitic acid, and citric acid reacts with a mono-alcohol having 3 to 12 alkyl carbon atoms.

In addition, pressure in the batch reactor is configured such that the pressure at the early stage is 0.3 barg to 1.0 barg and the pressure at the latter stage is 0 barg to 0.5 barg, the pressure at the early stage is greater than the pressure at the latter stage, and the early and latter stages are divided based on any one of the time points when reaction conversion rate is 30% to 90%.

In the present description, the early stage of reaction may refer to any one of the time points among 30% to 90%, preferably 30% to 80%, 40% to 80%, or 50% to 80% of the conversion rate from the time when temperature starts to rise after reactants are put into a reactor, whereas the latter stage of reaction may refer to a point from the one time point defined above to the time when the reaction is completed. In this case, the completion of the reaction may indicate that the residual amount of materials used as limited reactants out of polycarboxylic acid and mono-alcohol of reactants falls to a level of 1% or less with respect to the input amount, or the conversion rate of the reaction is at least 97% or more, preferably, 98% or more, or 99% or more. This considers that the reactants may be arbitrarily processed according to conditions through chemical engineering methods such as pressure reduction, pressurization, distillation, extraction, filtration, and the like depending on apparatuses and equipment conditions, and efficiency and product quality may be guaranteed only when processes are designed to make sure that reaction conversion rate reaches a level of 99% or more.

Hereinafter, a reaction applied to the preparation method according to an embodiment of the present invention will be described.

The preparation method of the present invention is a method for preparing an ester-based material, and may refer to a method in which an esterification reaction where a polyhydric carboxylic acid reacts with a mono-alcohol is applied.

Examples of the polyhydric carboxylic acid include at least one selected from the group consisting of terephthalic acid, phthalic acid, isophthalic acid, cyclohexane dicarboxylic acid, cyclohexane tricarboxylic acid, trimellitic acid, and citric acid. The polycarboxylic acid is one that includes the polycarboxylic acid itself, as well as a derivative thereof such as anhydride and acyl chloride, and for example, anhydrides such as terephthalic acid, phthalic acid, and isophthalic acid described above may also be used as the polycarboxylic acid of the present invention. The mono-alcohol applied herein is the one having 3 to 12 carbon atoms, and as long as the carbon number indicated herein is satisfied, the mono-alcohol may have a linear or branched alkyl group, and may be a mixture of linear and branched isomers, and the branched type may refer to a mixture containing at least one structural isomer. In implementing the performance of a plasticizer, the number of carbon atoms in the alkyl group of the mono-alcohol may vary depending on the use, and may be applied differently depending on which plasticizer is selected for blending, but the mono-alcohol may have preferably 4 to 10 carbon atoms, and at least one of the above alcohols may be used as the mono-alcohol.

An ester-based material prepared therethrough may be typically terephthalate, isophthalate, phthalate, cyclohexane 1,2-diester, cyclohexane 1,3-diester, cyclohexane 1,4-diester, cyclohexane 1,2,4-triester, trimellitate, or citrate, all of which are bonded with an alkyl group derived from the mono-alcohol.

In the preparation method according to an embodiment of the present invention, general conditions in the art may be applied to reaction temperature and duration at which a reaction may be performed as an esterification reaction, and the type and amount of a catalyst, and in some cases, may be suitably adjusted for process operation and applied.

An esterification reaction between the polycarboxylic acid and the mono-alcohol may occur at 120 to 250° C., preferably 140 to 230° C., more preferably 150 to 230° C. When the temperature is appropriately controlled in the above ranges, it may be preferable in terms of preventing catalyst degradation, improving reactivity, and energy efficiency.

According to an embodiment of the present invention, pressure in a reactor needs to be controlled in a certain range. Specifically, the reactor has an early stage pressure of 0.3 barg to 1.0 barg, and a latter stage pressure of 0 barg to 0.5 barg. In this case, pressure barg is a gauge pressure of a reactor without taking absolute pressure into account, and 0 barg may indicate a pressure equal to atmospheric pressure.

In the preparation method according to an embodiment of the present invention, the reaction temperature at which an esterification reaction is performed is a temperature equal to or above the boiling point of mono-alcohol, and as the reaction proceeds, a portion of the mono-alcohol is not involved in the reaction and thus is vaporized, and at the same time, water is generated as a reaction by-product and the water forms an azeotropic state with the mono-alcohol and is refluxed to an upper portion of the reactor. Such a reflux process is inevitable upon the esterification reaction, and how the reflux process is controlled may greatly affect reaction productivity and energy efficiency.

In such reaction conditions, when an esterification reaction is performed under pressure by increasing the pressure at the early stage of reaction, the vaporized alcohol may be retained at the site where the reaction takes place in the reactor to some extent, thereby leading to accelerated reaction rate and reduced reflux amount to increase energy efficiency.

As in the present invention, when the reaction is performed under pressure by increasing the pressure at the early stage as the pressure of the reactor is set to 0.3 barg to 1.0 barg, the vaporization of alcohol occurring at the beginning of reaction is suppressed to an appropriate level to induce reactions to proceed smoothly and to maintain the optimum reaction rate, and thus the issues described above are hardly seen.

However, when the pressure is set to less than 0.3 barg, the reflux of mono-alcohol is hardly suppressed, and thus a significant amount of alcohol is vaporized and refluxed, and this causes a great deal of energy use while a condenser and a bed separator are circulated from the reactor, and further due to such a reflux circulation, an absolute amount of alcohol required to be present and involved in the reaction is lost to deteriorate reactivity, and an additional input of alcohol to make up for the loss may cause an additional loss of energy, resulting in a continuous vicious cycle.

In addition, when the pressure is set to greater than 1.0 barg, reflux is suppressed as much as possible and the amount of alcohol present in the reactor increases, but at the same time, water generated as a reaction product also increases, thereby inducing a reverse reaction to reach a reversible reaction state at a certain level, causing a significant reduction in forward reaction rate. To prevent the above issues and increase reaction rate and energy efficiency, the pressure at the early stage of reaction may be controlled preferably to be 0.3 barg to 1.0 barg, preferably 0.4 to 1.0 barg, more preferably 0.5 to 0.9 barg, or 0.5 to 0.8 barg.

Meanwhile, the reaction under pressure as described above needs to be released at an appropriate time point. When the reaction is performed only under pressure upon the reaction process, water, a by-product of the reaction stays longer in the reactor, and when the water is not removed, the reaction may not be performed well in the forward reaction direction, resulting in reduced reaction rate. In addition, a catalyst is sensitive to water, and thus the catalyst may be deactivated. As such, the reaction pressure control in the esterification reaction does not solely bring about reaction improvement, but results in both improvement and deterioration together.

Accordingly, the time to release pressure may be selected in terms of preventing catalyst deactivation or reverse reaction activation caused by the presence of water, and reduced reaction rate due to an increase in the reflux amount of alcohol, and accordingly, the time point needs to be after at least 30% of the reaction conversion, and needs to be set at a level of no greater than 90% at most. That is, the early stage of reaction and latter stage of reaction are divided at the time between 30% to 90% of reaction conversion, preferably between 30% to 80%, more preferably between 40% to 80%, or between 50% to 80%. When the pressure of the reactor is lowered to an appropriate level at the time of such conversion rate, there is an advantage in that both energy saving and productivity improvement may be achieved.

The reactor pressure at the latter stage of reaction after this point is set down to 0 barg to 0.5 barg. In this case, the pressure at the latter stage of reaction needs to be less than the pressure at the early stage of reaction, and may preferably be 0 barg to 0.4 barg. The reactor pressure at the latter stage of reaction is set to be at least atmospheric pressure or higher, but it may be meaningful to be lower than the pressure at the early stage of reaction. As such, when the pressure is released at the latter stage of reaction, it may be effective to remove a certain amount of generated water, and due to the input of an excess amount of mono-alcohol, the amount of mono-alcohol remaining in the reactor may be higher than the equivalent even when a certain portion thereof is refluxed, and thus, the removal of water may make a more significant contribution. In addition, as a catalyst serves a more important role towards the latter stage of reaction, preventing deactivation of the catalyst while continuously removing water may also be critical.

Meanwhile, in addition, the pressure at the latter stage may be controlled to gradually decrease as the reaction proceeds. For example, after the pressure is reduced from the pressure at the early stage to the pressure at the latter stage, as the reaction proceeds, the pressure at the latter stage may be controlled to become lower, and in this case, the pressure may be gradually lowered in the range of 0 barg to 0.5 barg described above. More specifically, the pressure at the latter stage may be controlled to start at 0.4 barg, go through 0.2 barg, and be down to atmospheric pressure. As such, when the pressure is controlled to be further lowered, there is an advantage in that the stability of the process may be promoted by lowering the pressure at the latter stage of reaction, which requires relatively less pressurization.

Through the pressure control of reactors as such, productivity may be increased due to improved reaction rate and reduced conversion time to peak, and energy use is minimized to promote process efficiency.

Meanwhile, according to an embodiment of the present invention, the raw materials input to the preparation of the ester-based material is a polycarboxylic acid and a mono-alcohol as described above, and the reaction occurs theoretically in a molar ratio of 1 mol of carboxyl group to 1 mol of hydroxy group. More specifically, when the polycarboxylic acid is a dicarboxylic acid, the reaction between the dicarboxylic acid and the mono-alcohol occurs in a molar ratio of 1:2, and when the polycarboxylic acid is a tricarboxylic acid, the reaction between the tricarboxylic acid and the mono-alcohol occurs in a molar ratio of 1:3. Accordingly, the theoretical amount of carboxylic acid and mono-alcohol added as raw materials may be in a molar ratio of 1:2 to 1:8 with respect to divalent to tetravalent carboxylic acids.

This molar ratio is within the range that satisfies a minimum amount required for the reaction, and prevents energy loss due to unnecessary reflux caused by excessive alcohol input, and considering the excess amount of alcohol required in terms of achieving conversion rates of the reaction and controlling minimum residence time, the mono-alcohol may be added in an excess amount of 20 mol % to 100 mol % relative to the polycarboxylic acid equivalent. In the present invention, that the mono-alcohol is added in excess relative to the polycarboxylic acid equivalent indicates that greater than the amount of the mono-alcohol required to make the entire amount of the polycarboxylic acid react, that is an excess amount of mono-alcohol relative to the equivalent is added. More specifically, for example, that the mono-alcohol is added in more than 60 mol % relative to the polycarboxylic acid equivalent indicates that the mono-alcohol is added in 160 mol % of the equivalent. In the present invention, the amount of mono-alcohol added in excess may be 20 mol % or more, 30 mol % or more, 40 mol % or more, or 50 mol % or more, and may be 100 mol % or less, 90 mol % or less, 80 mol % or less, or 70 mol % or less relative to the polycarboxylic acid equivalent. When the excess amount of mono-alcohol is within the ranges described above, effects resulting from pressure control as described above may be maximized. Specifically, in applying the preparation method of the present invention, when the amount of mono-alcohol added in excess is 20 mol % to 40 mol % relative to the polycarboxylic acid equivalent, energy use may be improved to maximum, and when the amount thereof is 40 mol % to 100 mol %, productivity may also be further improved to maximum.

In addition, the mono-alcohol is input in excess, and thus, other than being input before the beginning of reaction, the mono-alcohol may be input also during the reaction. Therefore, the preparation method of the present invention may further include adding an addition amount of the mono-alcohol in the course of reactions. There is a benefit that when the mono-alcohol is not entirely input before the start of reaction, but is input in portions during the reaction at an appropriate time point, unnecessary energy use to heat the excess alcohol input at the beginning of reaction may be reduced. However, when the alcohol input is divided as such, the initial reaction rate may be lower than when the entire amount is added at the start of the reaction because the amount of the initial alcohol is relatively small compared to the case where the entire amount is added before the start of reaction. Therefore, additional input of mono-alcohol during the reaction and the amount thereof is preferable determined considering the balance between the reaction rate and the energy use.

When the mono-alcohol is additionally input during the reaction, the time point may be when the conversion rate reaches 20% or more or 30% or more, and 60% or less, or 50% or less. When the mono-alcohol is additionally input at an excessively early stage, the advantage of additional input of mono-alcohol as described above is not achievable, whereas when the mono-alcohol is additionally input at an excessively latter stage, the effect of improving the reaction rate according to the additional input of mono-alcohol may be insignificant because already little polycarboxylic acid remains.

The catalyst used in the preparation method of the present invention may be at least one selected from an acid catalyst such as sulfuric acid, hydrochloric acid, phosphoric acid, nitric acid, para-toluenesulfonic acid, methanesulfonic acid, ethanesulfonic acid, propanesulfonic acid, butanesulfonic acid, alkyl sulfuric acid, metal salt such as aluminum lactate, lithium fluoride, potassium chloride, cesium chloride, calcium chloride, iron chloride, and aluminum phosphate, metal oxide such as heteropolyacid, natural/synthetic zeolite, cation and anion exchange resin, and organic metal such as tetraalkyl titanate and a polymer thereof, and may preferably be tetraalkyl titanate. Examples of the tetraalkyl titanate include TiPT, TnBT, TEHT, and the like. As such, it is preferable to use tetraalkyl titanate as a catalyst, because catalyst by-products that may be generated in subsequent processes are controlled or not generated.

The amount of catalyst to be used may vary depending on the type of catalyst, and for example, a homogeneous catalyst may be used in an amount of 0.01 to 5 parts by weight, 0.01 to 3 parts by weight, 0.1 to 1 parts by weight, 0.1 to 0.5 parts by weight, or 0.1 to 0.3 parts by weight with respect to 100 parts by weight of polycarboxylic acid, and a heterogeneous catalyst may be used in an amount of 5 to 200 parts by weight, 5 to 100 parts by weight, 20 to 200 parts by weight, or 20 to 150 parts by weight with respect to 100 parts by weight of polycarboxylic acid. When the amount of the catalyst used is too small, catalyst activity itself is small and the reaction may not proceed well, and when the amount of the catalyst used is too large, in addition to an increase in catalyst cost, an excessive catalyst rather causes a reverse reaction, which may lead to reduced final conversion rate.

In addition, the catalyst may be introduced at one or more points before and during the initiation of reaction, and more specifically, the catalyst may be introduced both before the reaction initiation and during the reaction. When the catalyst is added not only before the initiation of the reaction as described above, but also during the reaction, the reaction rate may be increased even during the reaction to minimize the reaction duration.

Hereinafter, a process to which the preparation method is applied will be described with reference to the accompanying drawings.

According to an embodiment of the present invention, the method for preparing an ester-based material includes a column (stripper), a bed separator, and a condenser for building a batch reactor and a reflux system, and may also include a heat exchanger in some cases.

FIG. 1 shows reaction unit 10 in which an esterification reaction is performed according to the present invention, and the reaction unit 10 may include: a reactor 11 in which an esterification reaction of a polycarboxylic acid with mono-alcohol is performed; a column 12 in which mono-alcohol and water vaporized upon the esterification reaction are introduced from the reactor to perform gas-liquid separation, and liquid is fed into the reactor at a lower portion and gas is discharged from the top; a condenser 19 liquefying the gas discharged from the top of the column, which is then converted into a liquid mixture; and a layer separator 13 in which the liquid mixture is layer-separated into an organic layer and an aqueous layer, and the separated organic layer is fed to an upper end of the column.

More specifically, polyhydric carboxylic acid and mono-alcohol are fed through a raw material input line 11$b$ to perform an esterification reaction, and as for the raw material input line 11$b$, a pre-mixer (not shown) may be further installed upstream to supply raw materials to the reactor, a single raw material input line 11$b$ may perform line mixing to supply raw materials, or different input lines for each raw material may serve the supply. The input method of raw materials is not particularly limited as long as the method is capable of supplying raw materials to a reactor.

When reaction raw materials are supplied through the installation of the pre-mixer, the reaction raw materials may be preheated in the pre-mixer and then supplied, and in this case, a catalyst may be directly added into the reactor. In this case, there is an advantage in that side reactions generated between the catalyst and the reaction raw materials when the reaction raw materials and the catalyst are heated together up to the reaction temperature may be prevented.

In the reactor 11, as the reaction is performed, the mono-alcohol is involved in the reaction, but inevitably a portion of the mono-alcohol may not be involved in the reaction and vaporized as an esterification reaction takes place above the boiling point of the mono-alcohol, and accordingly, water other than the ester-based material is generated as a reaction product, vaporized together with the mono-alcohol, and move to the column 12 at the upper portion of the reactor 11, and in this case, may move through a gas discharge line 14.

In the column 12, the gaseous mono-alcohol and water introduced from the reactor 11 may be liquefied due to the liquid mono-alcohol fed to an upper end of the column 12 through an organic layer line 17 from the layer separator 13, and most of the gaseous mono-alcohol is selectively liquefied and the liquid mono-alcohol is fed back into the reactor 11 through a liquid inlet line 15, which may then be involved in the reaction again.

A portion of gaseous water and non-liquefied mono-alcohol may be introduced into the layer separator 13 from the upper end of the column 12 through a column upper line 16, in the layer separator, the mono-alcohol and water may be separated into an organic layer and an aqueous layer, respectively, the separated organic layer may be discharged to the column 12 through the organic layer line 17, and the aqueous layer may be discharged to the outside of the system through a aqueous layer line 18 or generated water may be utilized through various routes.

Meanwhile, in the layer separator 13, the liquid mono-alcohol and water are separated into layers, and in this regard, the gaseous mono-alcohol and water need to be liquefied in the layer separator 13 or before being fed into the layer separator 13. Accordingly, in the reaction unit of the preparation method according to an embodiment of the present invention, a condenser 19 is installed in the middle of the column upper line 16 connecting the column 12 and the layer separator 13, and the condenser 19 serves to remove heat from gaseous mono-alcohol and water, which are then liquefied before the input to layer separator 13.

In addition, in the preparation method of the present invention, the catalyst may be added through at least one selected from the reactor 11, the pre-mixer, and the liquid from the column. The introduction of the catalyst through such a path may minimize the amount of catalyst that is unnecessarily lost.

EXAMPLES

Hereinafter, the present invention will be described in more detail with reference to Examples. However, the following Examples are for illustrative purposes only to describe the present invention and are not intended to limit the scope of the present invention.

Materials and Equipment

Phthalic acid was used as polycarboxylic acid, 2-ethylhexanol was used as mono-alcohol, and tetrabutyl titanate was used as a catalyst. As a reactor for performing a reaction, a batch reactor provided with a reflux facility was used.

Examples and Comparative Examples

An esterification reaction of phthalic acid and 2-ethylhexanol was performed using the materials and equipment described above. In each Example and Comparative Example, applying pressure and/or pressure release were performed with respect to a specific time point, or control such as adding 2-ethylhexanol or a catalyst was performed, and according to controlled conditions, Examples and Comparative Examples were divided into groups and outlined below. Meanwhile, the amount of alcohol added in excess in this Example and Comparative Example is a value corresponding to the mole % of 2-ethylhexanol added in excess relative to the phthalic acid equivalent, and for example, when 320 mol of 2-ethylhexanol is added relative to 100 mol of phthalic acid, 120 mol of 2-ethylhexanol is further added relative to the equivalent of 200 mol. In this case, the amount of excess alcohol is 120/200*100 mol %=60 mol %. In addition, a catalyst was added in an amount of 0.23 wt % relative to the added phthalic acid. In addition, in this Example and Comparative Example, the pressure release time indicates the time taken from the initiation of reaction, and a blank area in the table indicates omission of measurement.

Group 1. Confirmation of Effect of Applying Pressure and Pressure Release Control Phthalic acid, 2-ethylhexanol, and tetrabutyl titanate as a catalyst were put into a batch reactor, and an esterification reaction was performed by heating the batch reactor. In each case, adjusting the amount of excess alcohol, increasing initial reaction pressure, or adjusting pressure release time, and the like were performed, and specific conditions were outlined as follows.

TABLE 1

| | Excess input amount of alcohol (mol %) | Early stage pressure (barg) | Latter stage pressure (barg) | Pressure release time (min) |
|---|---|---|---|---|
| Comparative Examples 1-1 | 60 | Atmospheric pressure | Atmospheric pressure | — |
| Comparative Examples 1-2 | 60 | 0.8 | 0.8 | — |

TABLE 1-continued

| | Excess input amount of alcohol (mol %) | Early stage pressure (barg) | Latter stage pressure (barg) | Pressure release time (min) |
|---|---|---|---|---|
| Example 1-1 | 60 | 0.8 | 0.2 | 180 |
| Example 1-2 | 60 | 0.8 | Atmospheric pressure | 180 |
| Example 1-3 | 60 | 0.8 | Atmospheric pressure | 300 |
| Reference Example 1-1 | 0 | Atmospheric pressure | Atmospheric pressure | — |
| Reference Example 1-2 | 0 | 0.8 | 0.8 | — |

Table 2 shows the temperature inside the reactors over time in Comparative Examples, Examples, and Reference Examples of Table 1, and Table 3 shows the conversion rates. Meanwhile, the conversion rates were calculated by measuring the cumulative generated water mass up to each time, and dividing the measured cumulative generated water mass by theoretical generated water mass generated when 100% conversion is achieved, and measurements and calculations were made from 120 minutes after the initiation of the reaction, which is the point at which the generated water was confirmed in earnest.

TABLE 2

| | Temperature inside reactor (° C.) | | | | | | |
|---|---|---|---|---|---|---|---|
| Time (min) | Comparative Examples 1-1 | Comparative Examples 1-2 | Example 1-1 | Example 1-2 | Example 1-3 | Reference Example 1-1 | Reference Example 1-2 |
| 10 | 43 | 42 | 42 | 44 | 43 | 45 | 39 |
| 20 | 64 | 62 | 62 | 64 | 63 | 69 | 63 |
| 30 | 78 | 77 | 77 | 77 | 78 | 83 | 80 |
| 40 | 100 | 100 | 99 | 99 | 99 | 107 | 107 |
| 50 | 121 | 121 | 120 | 120 | 120 | 128 | 128 |
| 60 | 135 | 135 | 135 | 135 | 133 | 146 | 145 |
| 70 | 157 | 155 | 157 | 157 | 154 | 172 | 172 |
| 80 | 176 | 178 | 179 | 178 | 177 | 177 | 186 |
| 90 | 179 | 190 | 187 | 189 | 187 | 182 | 196 |
| 100 | 183 | 198 | 196 | 198 | 196 | 183 | 203 |
| 110 | 184 | 204 | 204 | 204 | 203 | 183 | 204 |
| 120 | 185 | 205 | 205 | 205 | 202 | 184 | 204 |
| 150 | 186 | 210 | 208 | 208 | 208 | 187 | 211 |
| 180 | 189 | 215 | 204 (Pressure reduction) | 203 (Pressure reduction) | 213 | 190 | 216 |
| 210 | 190 | 217 | 204 | 199 | 217 | 195 | 220 |
| 240 | 194 | 222 | 204 | 200 | 221 | 200 | 224 |
| 270 | 197 | 224 | 208 | 203 | 224 | 206 | 228 |
| 300 | 199 | 228 | 210 | 204 | 227 (Pressure reduction) | 214 | 231 |
| 330 | 206 | 232 | 215 | 206 | 210 | 221 | 234 |
| 360 | 212 | 234 | 219 | 208 | 209 | 228 | — |
| 380 | — | | 222 | 211 | — | — | — |
| 390 | — | 237 | — | 211 | 209 | — | — |
| 410 | — | 237 | — | — | — | — | — |
| 430 | — | — | — | — | 211 | — | — |

TABLE 3

| Time (min) | Comparative Examples 1-1 | Comparative Examples 1-2 | Example 1-1 | Example 1-2 | Example 1-3 | Reference Example 1-1 | Reference Example 1-2 |
|---|---|---|---|---|---|---|---|
| | | | | Conversion rate (%) | | | |
| 120 | 12.42 | 17.04 | 17.04 | 17.39 | 13.84 | 13.13 | 14.20 |
| 150 | 21.65 | 36.92 | 35.50 | 35.85 | 31.24 | 23.43 | 25.56 |
| 180 | 34.08 | 52.18 | 50.05 (Pressure reduction) | 50.76 (Pressure reduction) | 47.21 | 33.72 | 37.27 |
| 210 | 45.44 | 62.12 | 60.35 | 60.70 | 59.64 | 44.04 | 40.82 |
| 240 | 56.44 | 70.64 | 69.93 | 71.35 | 68.87 | 52.89 | 45.79 |
| 270 | 68.87 | 79.16 | 78.10 | 77.03 | 77.03 | 59.28 | 51.12 |
| 300 | 80.58 | 85.55 | 86.61 | 83.42 | 82.71 (Pressure reduction) | 68.16 | 53.60 |
| 330 | 93.36 | 91.23 | 93.00 | 88.74 | 89.10 | 74.55 | 56.80 |
| 360 | 98.33 | 95.13 | 97.62 | 94.42 | 92.29 | 76.68 | 56.80 |
| 380 | — | — | 98.68 | 96.55 | — | 76.68 | 56.80 |
| 390 | — | 97.62 | — | 97.62 | 96.55 | — | — |
| 410 | — | 99.04 | — | — | — | — | — |
| 430 | — | — | — | — | 98.33 | — | — |

As shown in Tables 2 and 3 above, it is confirmed that in Examples 1-1 and 1-2 in which the reaction was initiated under pressure, but the pressure was released or reduced at the time of about 50% conversion, a high conversion rate was achieved at a faster time than in Comparative Examples and Reference Examples, and the temperature inside the reactor at the time when the final conversion was achieved was also in the ideal temperature range of 210 to 230° C., thereby minimizing energy loss during the reaction.

On the other hand, in Comparative Example 1-1 in which no pressure was applied, as a large amount of alcohol was vaporized during the reaction, the conversion rate increased slowly compared to Example, and the final conversion rate also showed a lower value than Example. This indicates that a significant portion of the vaporized alcohol was not involved in the reaction again, resulting in loss of raw materials, and thus, a desired ester-based compound is not sufficiently prepared. In addition, in Comparative Example 1-2 in which pressure was applied and maintained until the end of reaction without pressure reduction during the reaction, as the vaporized alcohol was pressurized to be involved in the reaction again after liquefaction, the conversion rate increased faster than in Comparative Example 1-1, but the temperature inside the reactor became higher than the preferred range as the amount of liquefied alcohol remained relatively high even after the middle of the reaction in which phthalic acid was consumed to some extent. This may contribute to deterioration of product quality obtained when the final conversion rate is achieved.

In addition, it was confirmed that in Reference Examples 1-1 and 1-2 in which the alcohol was not input in excess, but was input according to the equivalent, and pressure reduction was not performed after pressurization, a large amount of alcohol vaporization occurred during the reaction, resulting in insufficient amount of alcohol to be involved in the reaction, and thus, the conversion rate did not increase above a certain value and stayed still. This means that the desired reaction was not sufficiently achieved, indicating that, in the esterification reaction carried out in the present invention, an excess of alcohol needs to be input to achieve a sufficient conversion rate.

Group 2. Confirmation of Effect According to Catalyst Input/Split Input

It was performed in the same manner as in Example of Group 1, except that when the amount of catalyst (0.23 wt % relative to phthalic acid) initially input in Example of Group 1 is 100%, in addition to the catalyst input of 100%, the catalyst was additionally input thereafter, or the 100% catalyst input was divided. Specific conditions for each case are outlined in Table 4 below.

TABLE 4

| | Excess input amount of alcohol (mol %) | Early stage pressure (barg) | Latter stage pressure (barg) | Pressure release time (min) | Initial catalyst Input (%) | Additional input of catalyst (%)/Time (min) |
|---|---|---|---|---|---|---|
| Example 2-1 | 60 | 0.8 | Atmospheric pressure | 150 | 100 | 100%/ 180 min. |
| Example 2-2 | 60 | 0.8 | Atmospheric pressure | 150 | 100 | 1) 100%/ 120 min. 2) 100%/ 240 min. |
| Example 2-3 | 40 | 0.8 | Atmospheric pressure | 270 | 100 | 100%/ 300 min. |
| Example 2-4 | 40 | 0.8 | Atmospheric pressure | 270 | 50 | 50%/ 270 min. |

In addition, in the same manner as in Group 1 above, the temperatures inside the reactors and conversion rates over time in Examples of Table 4 above are outlined in Table 5.

TABLE 5

| Time (min) | Example 2-1 Temperature (° C.) | Example 2-1 Conversion rate (%) | Example 2-2 Temperature (° C.) | Example 2-2 Conversion rate (%) | Example 2-3 Temperature (° C.) | Example 2-3 Conversion rate (%) | Example 2-4 Temperature (° C.) | Example 2-4 Conversion rate (%) |
|---|---|---|---|---|---|---|---|---|
| 10 | 42 | | 45 | | 44 | | 41 | |
| 20 | 63 | | 62 | | 65 | | 64 | |
| 30 | 77 | | 77 | | 80 | | 79 | |
| 40 | 100 | | 99 | | 106 | | 102 | |
| 50 | 121 | | 135 | | 125 | | 124 | |
| 60 | 134 | | 157 | | 140 | | 137 | |
| 70 | 158 | | 178 | | 166 | | 157 | |
| 80 | 179 | | 183 | | 185 | | 178 | |
| 90 | 189 | | 189 | | 195 | | 197 | |
| 100 | 198 | | 197 | | 202 | | 201 | |
| 110 | 204 | | 204 | | 204 | | 201 | |
| 120 | 204 | 14.91 | 204 | 16.33 | 205 | 20.59 | 204 | 15.97 |
| 150 | 207 (Pressure reduction) | 31.24 | 210 (Pressure reduction) | 38.34 | 211 | 36.21 | 206 | 30.88 |
| 180 | 194 | 41.53 | 215 | 52.18 | 217 | 48.99 | 210 | 45.08 |
| 210 | 193 | 56.09 | 219 | 60.35 | 219 | 58.57 | 214 | 59.64 |
| 240 | 194 | 67.80 | 222 | 68.87 | 223 | 67.09 | 220 | 74.19 |
| 270 | 199 | 77.74 | 225 | 79.52 | 227 (Pressure reduction) | 72.77 | 226 (Pressure reduction) | 78.81 |
| 300 | 203 | 86.61 | 227 | 84.13 | 205 | 82.00 | 207 | 85.19 |
| 330 | 207 | 94.42 | | | 211 | 89.45 | 211 | 94.07 |
| 335 | | | 230 | 90.87 | | | | |
| 340 | 208 | 97.26 | | | | | | |
| 360 | 211 | 99.99 | 232 | 95.13 | 215 | 94.78 | 218 | 98.68 |
| 380 | | | | | 218 | 97.62 | | |
| 390 | | | 236 | 97.62 | | | | |
| 400 | | | | | 220 | 99.04 | | |
| 410 | | | | | — | 99.39 | | |

As seen in Table 5, Examples 2-1 to 2-3, in which the catalyst was additionally input, all showed high final conversion rates. In addition, when comparing Examples 2-1 and 2-2 in which 100% of the catalyst was input or 200% of the catalyst was input in the same conditions, in Example 2-1, in which 100% of the catalyst was input only once at 180 minutes, a high conversion rate was achieved in a faster time, whereas in Example 2-2 in which 100% of the catalyst was additionally input at 120 minutes and 240 minutes each, the reaction more than necessary was activated according to the excess catalyst, which led to an increase in temperature inside the reactor to probably cause the conversion rate to increase rather later than in Example 2-1. In addition, when comparing Example 2-3 in which the pressure was reduced at the same time point, but the catalyst was additionally input with Example 2-4 in which the catalyst input was divided, it was confirmed that the temperature inside the reactor increased similarly, but the final conversion rate was higher in Example 2-3 with greater catalyst input. This suggests that an increase in catalyst input may lead to an improvement in conversion rate. However, as seen from the comparison of Examples 2-1 and 2-2 described above, an excessive increase in the input amount of catalyst may have a rather adverse effect, and thus, the amount of catalyst input may need to be determined within an appropriate range.

Group 3. Confirmation of Effect According to the Input Amount of Alcohol

It was performed in the same manner as in Example of Group 1, except that the amount of excess alcohol was adjusted, and a catalyst corresponding to 100% was additionally input during the reaction. Specific conditions for each case are outlined in Table 6 below.

TABLE 6

| | Excess input amount of alcohol (mol %) | Early stage pressure (barg) | Latter stage pressure (barg) | Pressure release time (min) | Additional input time of catalyst (min) |
|---|---|---|---|---|---|
| Example 3-1 | 60 | 0.8 | Atmospheric pressure | 270 | 300 |
| Example 3-2 | 50 | 0.8 | Atmospheric pressure | 270 | 300 |
| Example 3-3 | 40 | 0.8 | Atmospheric pressure | 270 | 300 |
| Example 3-4 | 60 | 0.6 | Atmospheric pressure | 270 | 270 |
| Example 3-5 | 40 | 0.6 | Atmospheric pressure | 270 | 270 |

In addition, in the same manner as in Group 1 above, the temperatures inside the reactors and conversion rates over time in Examples of Table 6 above are outlined in Table 7.

TABLE 7

| Time (min) | Example 3-1 Temperature (° C.) | Example 3-1 Conversion rate (%) | Example 3-2 Temperature (° C.) | Example 3-2 Conversion rate (%) | Example 3-3 Temperature (° C). | Example 3-3 Conversion rate (%) | Example 3-4 Temperature (° C.) | Example 3-4 Conversion rate (%) | Example 3-5 Temperature (° C.) | Example 3-5 Conversion rate (%) |
|---|---|---|---|---|---|---|---|---|---|---|
| 10 | 45 | | 36 | | 44 | | 35 | | 41 | |
| 20 | 62 | | 58 | | 65 | | 57 | | 64 | |
| 30 | 77 | | 76 | | 80 | | 73 | | 79 | |
| 40 | 99 | | 104 | | 106 | | 94 | | 103 | |
| 50 | 121 | | 124 | | 125 | | 117 | | 124 | |
| 60 | 135 | | 139 | | 140 | | 133 | | 137 | |
| 70 | 156 | | 163 | | 166 | | 152 | | 164 | |
| 80 | 178 | | 180 | | 185 | | 176 | | 181 | |
| 90 | 190 | | 194 | | 195 | | 187 | | 191 | |
| 100 | 197 | | 201 | | 202 | | 195 | | 198 | |
| 110 | 203 | | 203 | | 204 | | 198 | | 202 | |
| 120 | 202 | 18.46 | 205 | 21.65 | 205 | 20.59 | 200 | 17.75 | 202 | 19.52 |
| 150 | 209 | 36.56 | 211 | 39.40 | 211 | 36.21 | 203 | 36.56 | 205 | 36.92 |
| 180 | 213 | 52.18 | 217 | 53.46 | 217 | 48.99 | 209 | 53.60 | 210 | 51.83 |
| 210 | 218 | 63.90 | 220 | 62.83 | 219 | 58.57 | 214 | 68.87 | 216 | 62.83 |
| 240 | 222 | 73.48 | 224 | 71.71 | 223 | 67.09 | 219 | 75.97 | 220 | 71.35 |
| 270 | 219 | 81.29 | 228 | 77.03 | 227 | 72.77 | 223 | 83.77 | 225 | 77.39 |
| | (Pressure reduction) | | (Pressure reduction) | | (Pressure reduction) | | (Pressure reduction) | | (Pressure reduction) | |
| 300 | 205 | 90.52 | 206 | 84.84 | 205 | 82.00 | 205 | 91.94 | 209 | 85.19 |
| 330 | 209 | 97.26 | 210 | 93.36 | 211 | 89.45 | 211 | 97.26 | 214 | 93.36 |
| 340 | 211 | 98.33 | | | | | | | | |
| 350 | | | 213 | 96.55 | | | | | | |
| 360 | | | | | 215 | 94.78 | | | 219 | 97.97 |
| 370 | | | 216 | 99.04 | | | | | | |
| 380 | | | | | 218 | 97.62 | | | 223 | 99.39 |
| 400 | | | | | 220 | 99.04 | | | | |
| 410 | | | | | — | 99.39 | | | | |

As shown in Table 7, it was confirmed that when only the input amount of alcohol is adjusted in the same conditions, greater alcohol input leads to greater amount of alcohol involved in the reaction, thereby resulting in a rapid increase in conversion rate. However, greater alcohol input requires greater energy use for heating the excess alcohol. Therefore, it is preferable to determine an appropriate input amount of alcohol within the scope of the present invention considering target reaction completion time, energy use, and the like.

Group 4. Confirmation of Effect According to Additional Input of Alcohol and Catalyst It was performed in the same manner as in Example of Group 1, except that a portion of excess alcohol was input during the reaction, and a catalyst was also additionally input during the reaction. Specific conditions for each case are outlined in Table 8 below.

In addition, in the same manner as in Group 1 above, the temperatures inside the reactors and conversion rates over time in Examples of Table 8 are outlined in Table 9.

TABLE 9

| Time (min) | Example 4-1 Temperature (° C.) | Example 4-1 Conversion rate (%) | Example 4-2 Temperature (° C.) | Example 4-2 Conversion rate (%) |
|---|---|---|---|---|
| 10 | 46 | | 43 | |
| 20 | 66 | | 66 | |
| 30 | 80 | | 82 | |
| 40 | 102 | | 102 | |
| 50 | 125 | | 125 | |
| 60 | 138 | | 138 | |
| 70 | 162 | | 159 | |
| 80 | 180 | | 179 | |

TABLE 8

| | Excess input amount of alcohol (Initial input/ Intermediate input, mol %) | Intermediate input time of alcohol (min) | Early stage pressure (barg) | Latter stage pressure (barg) | Pressure release time (min) | Additional input of catalyst (%) | Additional input time of catalyst (min) |
|---|---|---|---|---|---|---|---|
| Example 4-1 | 20 20 | 180 | 0.8 | Atmospheric pressure | 270 | 100 | 270 |
| Example 4-2 | 20 20 | 180 | 0.5 | Atmospheric pressure | 270 | 100 | 270 |

TABLE 9-continued

| | Example 4-1 | | Example 4-2 | |
|---|---|---|---|---|
| Time (min) | Temper-ature (° C.) | Conversion rate (%) | Temper-ature (° C.) | Conversion rate (%) |
| 90 | 193 | | 189 | |
| 100 | 201 | | 197 | |
| 110 | 205 | | 195 | |
| 120 | 205 | 13.13 | 197 | 12.07 |
| 150 | 210 | 28.40 | 202 | 24.85 |
| 180 | 215 | 39.76 | 206 | 38.69 |
| 210 | 217 | 50.05 | 214 | 48.28 |
| 240 | 220 | 58.57 | 219 | 57.86 |
| 270 | 225 | 65.67 | 222 | 65.32 |
| | (Pressure reduction) | | (Pressure reduction) | |
| 300 | 202 | 74.19 | 202 | 74.55 |
| 330 | 206 | 83.07 | 206 | 83.42 |
| 360 | 211 | 89.81 | 211 | 89.81 |
| 390 | 216 | 94.78 | 215 | 95.49 |
| 420 | 219 | 98.33 | 219 | 97.62 |
| 430 | 220 | 99.39 | | |

As shown in Table 9, It was confirmed that even when the excess alcohol was not input all at once before the initiation of reaction, but was input during the reaction, using the preparation method of the present invention, which applies pressure at the initiation of reaction and releases pressure during the reaction, a desired ester-based material was possibly prepared at a high conversion rate.

Group 5. Confirmation of Effect According to Additional Control of Latter Stage Pressure It was performed in the same manner as in Example of Group 1, except that after performing pressure reduction from early stage pressure to latter stage pressure, the latter stage pressure was further reduced. Specific conditions for each case are outlined in Table 10 below.

TABLE 10

| | Excess input amount of alcohol (mol %) | Early stage pressure (bar g) | Latter stage pressure and time of change (barg/min) | | | Initial input of catalyst (%) | Additional input of catalyst (%) | Intermediate input time of alcohol (min) |
|---|---|---|---|---|---|---|---|---|
| Example 5-1 | 40 | 0.5 | 0.4 (270) | 0.2 (330) | Atmos-pheric pressure (390) | 100 | 100 | 270 |

Specifically, in Example 5-1, the pressure was lowered from 0.8 barg to 0.4 barg at 270 minutes, then the pressure was further lowered to 0.2 barg at 330 minutes, and the pressure was lowered to atmospheric pressure at 390 minutes. In addition, in Example 5-1, 100% of the 200% catalyst was added at the initiation of reaction, and the remaining 100% was added at 270 minutes after the initiation of reaction.

In addition, in the same manner as in Group 1 above, the temperatures inside the reactors and conversion rates over time in Examples of Table 10 are outlined in Table 11.

TABLE 11

| | Example 5-1 | | |
|---|---|---|---|
| Time (min) | Temper-ature (° C.) | Conversion rate (%) | |
| 10 | 41 | | |
| 20 | 63 | | |
| 30 | 79 | | |
| 40 | 102 | | |
| 50 | 124 | | |
| 60 | 135 | | |
| 70 | 159 | | |
| 80 | 180 | | |
| 90 | 195 | | |
| 100 | 202 | | |
| 110 | 205 | | |
| 120 | 204 | 16.33 | |
| 150 | 208 | 32.30 | |
| 180 | 214 | 45.44 | |
| 210 | 219 | 56.44 | |
| 240 | 223 | 63.54 | |
| 270 | 226 | 71.35 | |
| | (Pressure reduction) | | |
| 300 | 221 | 77.74 | |
| 330 | 225 | 83.77 | |
| 360 | 220 | 88.39 | |
| 390 | 223 | 91.94 | |
| 420 | 217 | 94.78 | |
| 450 | 219 | 95.49 | |

As shown in Table 11, it was confirmed that even when the pressure at the latter stage of reaction was controlled in such a way that the pressure at the latter stage of reaction was not lowered all at once but was lowered slowly, a high conversion rate was achieved similarly to the case in which the pressure at the latter stage of reaction was lowered all at once. In addition, when the pressure is gradually changed as such, there is an advantage in that the stability of the process may be obtained compared to when the pressure is changed at once.

DESCRIPTION OF SYMBOLS

10 Reaction unit, 11: Reactor
11b Raw material input line
12: Column, 13: layer separator
14: Gas discharge line, 15: Liquid inlet line
16: Column upper portion line, 17: organic layer line
18: Aqueous line, 19: Condenser

The invention claimed is:

1. A method for preparing an ester-based material, the method comprising:

a step in which in a batch reactor, under a catalyst, at least one polycarboxylic acid selected from the group consisting of a terephthalic acid, a phthalic acid, an isophthalic acid, a cyclohexane dicarboxylic acid, a cyclohexane tricarboxylic acid, a trimellitic acid, and citric acid reacts with at least one mono-alcohol having 3 to 12 alkyl carbon atoms, wherein pressure in the reactor is configured such that the pressure at the early stage is 0.3 barg to 1.0 barg and the pressure at the latter stage is 0 barg to 0.5 barg, the pressure at the early stage being greater than the pressure at the latter stage, and the early and latter stages are divided based on any one of the time points when a degree of conversion of the polycarboxylic acid is 30% to 90%.

2. The method of claim 1, wherein the batch reactor has an early stage pressure of 0.4 barg to 1.0 barg, and a latter stage pressure of 0 barg to 0.4 barg.

3. The method of claim 1, wherein the mono-alcohol is added in excess of 20 mol % to 100 mol % relative to polycarboxylic acid equivalent.

4. The method of claim 1, wherein:

the reaction is performed in the presence of a catalyst; and the catalyst is added at one or more time points before the initiation of the reaction and in the course of the reaction.

5. The method of claim 4, wherein the catalyst is added before the initiation of the reaction and in the course of the reaction.

6. The method of claim 1, wherein the latter stage pressure gradually decreases as reactions proceed.

7. The method of claim 1, further comprising adding an additional amount of the mono-alcohol in the course of reactions.

8. The method of claim 1, wherein the preparation method is performed in a reaction unit comprising:

a reactor in which an esterification reaction of a polycarboxylic acid with a mono-alcohol is performed;

a column in which the mono-alcohol and water vaporized upon the esterification reaction are introduced from the reactor to perform gas-liquid separation, and liquid is fed into the reactor at a lower portion and gas is discharged from the top;

a condenser liquefying the gas discharged from the top of the column, which is then converted into a liquid mixture; and a layer separator in which the liquid mixture is layer-separated into an organic layer and an aqueous layer, and the separated organic layer is fed to an upper end of the column.

9. The method of claim 8, wherein:

the reaction unit further comprises a pre-mixer placed upstream of the reactor; and the polycarboxylic acid and the mono-alcohol are fed into to the pre-mixer, mixed and preheated, and then transferred to the reactor.

10. The method of claim 9, wherein the catalyst is added through at least one selected from among the reactor, the pre-mixer, and the liquid from the column.

* * * * *